United States Patent
Jeong et al.

(10) Patent No.: US 10,334,712 B2
(45) Date of Patent: Jun. 25, 2019

(54) RADIOGRAPHY APPARATUS

(71) Applicant: ELECTRONICS AND TELECOMMUNICATIONS RESEARCH INSTITUTE, Daejeon (KR)

(72) Inventors: Jin-Woo Jeong, Daejeon (KR); Yoon-Ho Song, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 300 days.

(21) Appl. No.: 15/273,486

(22) Filed: Sep. 22, 2016

(65) Prior Publication Data

US 2017/0135189 A1    May 11, 2017

(30) Foreign Application Priority Data

Nov. 11, 2015  (KR) .................. 10-2015-0158223
Jun. 29, 2016  (KR) .................. 10-2016-0081868

(51) Int. Cl.
```
H05G 1/08     (2006.01)
H05G 1/30     (2006.01)
H01J 35/06    (2006.01)
H01J 35/08    (2006.01)
H01J 35/14    (2006.01)
H05G 1/10     (2006.01)
```
(52) U.S. Cl.
CPC .............. *H05G 1/30* (2013.01); *H01J 35/06* (2013.01); *H01J 35/08* (2013.01); *H01J 35/14* (2013.01); *H05G 1/10* (2013.01)

(58) Field of Classification Search
CPC .. H05G 1/00; H05G 1/10; H05G 1/30; H05G 1/56; H05G 1/60; H01J 35/00; H01J 35/06; H01J 35/08; H01J 35/14; H01J 35/045; H01J 35/025; H01J 35/065; A61B 6/4007; A61B 6/4014; A61B 6/542; A61B 6/405
USPC .... 378/4, 9, 16, 62, 101, 109, 113, 122, 138
See application file for complete search history.

(56) References Cited

U.S. PATENT DOCUMENTS

| | | | |
|---|---|---|---|
| 8,212,487 B2 | 7/2012 | Jeong et al. | |
| 8,649,479 B2 | 2/2014 | De Man et al. | |
| 8,705,822 B2 * | 4/2014 | Yu | G06T 11/006 378/5 |
| 2013/0030288 A1 | 1/2013 | Lee et al. | |
| 2013/0271037 A1 * | 10/2013 | Jeong | H05B 41/14 315/307 |

(Continued)

FOREIGN PATENT DOCUMENTS

| | | | |
|---|---|---|---|
| KR | 10-2011-0033762 A | 3/2011 | |
| KR | 10-2014-0143399 A | 12/2014 | |
| WO | WO 2013/136299 A1 | 9/2013 | |

*Primary Examiner* — Jurie Yun

(57) ABSTRACT

Provided herein is a radiography apparatus including an X-ray source configured to irradiate a subject radiation, and a sensing module configured to sense the radiation having passed through the subject, wherein the X-ray source includes a cathode electrode comprising an electric field emitting source configured to emit electrons, an anode electrode disposed opposite to the cathode electrode and configured to use the electrons to generate the radiation, and a current control unit connected to the cathode electrode to control an amount of the electrons.

16 Claims, 6 Drawing Sheets

(56) References Cited

U.S. PATENT DOCUMENTS

2016/0005565 A1   1/2016   Kang et al.

* cited by examiner

130

130'

RADIOGRAPHY APPARATUS

CROSS-REFERENCE TO RELATED APPLICATION

The present application claims priority to Korean Patent Application Numbers 10-2015-0158223 filed on Nov. 11, 2015 and 10-2016-0081868 filed on Jun. 29, 2016, in the Korean Intellectual Property Office, the entire disclosure of which is incorporated by reference herein.

BACKGROUND

Field of Invention

Various embodiments of the present disclosure relate to a radiography apparatus.

Description of Related Art

A radiography apparatus may be configured with an X-ray source for emitting X-rays while rotating around a subject and a sensing module for collecting shadow images generated when the X-rays pass the subject. The sensing module rotates around the subject in correspondence to rotation of the X-ray source, and when a shadow image of the subject is obtained by the X-ray source and the sensing module continuously rotating without stop, a moving blur phenomenon may occur.

Accordingly, in order to reduce the moving blur phenomenon caused by the rotational movement, the radiography apparatus repeats a process for stopping the X-ray source and the sensing module after rotation at a certain angle, obtaining a shadow image, and then rotating the X-ray source and the sensing module again at a certain angle.

SUMMARY

Various embodiments of the present disclosure are directed to a radiography apparatus for emitting radiation while rotating without stop to generate a subject's internal image in which a moving blur phenomenon is improved.

Furthermore, various embodiments of the present disclosure are directed to a radiography apparatus for using an X-ray tube as an electric field emitting source.

In addition, various embodiments of the present disclosure are directed to a radiography apparatus capable of varying energy to adjust the intensity of radiation.

One embodiment of the present disclosure provides a radiography apparatus including: an X-ray source configured to irradiate a subject radiation; and a sensing module configured to sense the radiation having passed through the subject, wherein the X-ray source includes: a cathode electrode including an electric field emitting source configured to emit electrons; an anode electrode disposed opposite to the cathode electrode and configured to use the electrons to generate the radiation; and a current control unit connected to the cathode electrode to control an amount of the electrons.

According to the embodiment, the X-ray source and the sensing module may rotate around the subject at every constant period.

According to the embodiment, the X-ray source may further include a gate electrode configured to induce emission of the electrons from the electric field emitting source.

According to the embodiment, the X-ray source may further include focusing gate electrode configured to focus the electrons emitted by the gate electrode.

According to the embodiment, the current control unit may include a switching transistor of which a first electrode is connected to the cathode electrode, a second electrode is connected to a ground power source, and a gate electrode receives a switching voltage.

According to the embodiment, the X-ray source may irradiate the subject with the radiation when the switching transistor is turned on.

According to the embodiment, the current control unit may further include a pull-up voltage source connected to the cathode electrode through a serially connected pull-up resistor to control an amount of the electrons.

According to the embodiment, the switching transistor may be driven in a saturation region according to a supply of the switching voltage.

According to the embodiment, the radiography apparatus may further include a power supply unit configured to supply an anode voltage to the anode electrode, wherein the power supply unit varies the anode voltage at every constant period.

According to the embodiment, the X-ray source and the sensing module may be disposed opposite to each other with the subject centered.

Another embodiment of the present disclosure provides a radiography apparatus including: a first X-ray source configured to irradiate a subject with first radiation; a second X-ray source separately disposed from the first X-ray source at a constant interval to irradiate the subject with second radiation; first sensing module configured to the first radiation having passed through the subject; and a second sensing module configured to the second radiation having passed through the subject, wherein each of the first X-ray source and the second X-ray source includes: a cathode electrode including an electric field emitting source configured to emit electrons; an anode electrode disposed opposite to the cathode electrode and configured to accelerate the electrons; and a current control unit connected to the cathode electrode to control an amount of the electrons.

According to the embodiment, each of the first X-ray source and the second X-ray source may further include: a gate electrode configured to induce emission of the electrons from the electric field emitting source; and a focusing gate electrode configured to focus the electrons emitted by the gate electrode.

According to the embodiment, the first X-ray source may emit the first radiation for a first period, and the second X-ray source emits the second radiation for a second period after the first period.

According to the embodiment, intensities of the first and second radiations may be different from each other.

According to the embodiment, the first X-ray source and the first sensing module may be disposed opposite to each other, and the second X-ray source and the second sensing module may be disposed opposite to each other.

Still another embodiment of the present disclosure provides a radiography apparatus including: a first X-ray source configured to irradiate a subject with first radiation; a second X-ray source separately disposed from the first X-ray source at a constant interval to irradiate the subject with second radiation; and a sensing module configured to sense the first and second radiations having passed through the subject, wherein each of the first X-ray source and the second X-ray source includes: a cathode electrode including an electric field emitting source configured to emit electrons; an anode electrode disposed opposite to the cathode electrode and configured to accelerate the electrons; and a current control unit connected to the cathode electrode and to control an amount of the electrons.

According to the embodiment, the first X-ray source and the second X-ray source may be disposed opposite to the sensing module.

BRIEF DESCRIPTION OF THE DRAWINGS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the drawing figures, dimensions may be exaggerated for clarity of illustration. It will be understood that when an element is referred to as being "between" two elements, it can be the only element between the two elements, or one or more intervening elements may also be present. Like reference numerals refer to like elements throughout.

DETAILED DESCRIPTION

Figure 1:
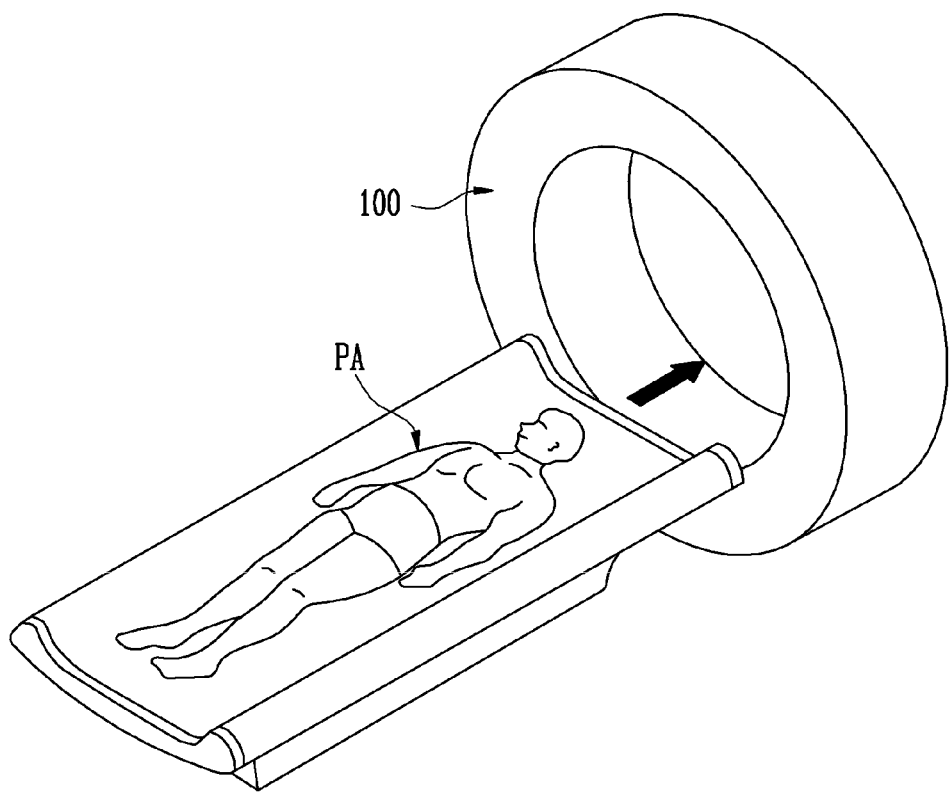
FIG. 1 is a drawing for explaining an operation of a radiography apparatus according to an embodiment of the present disclosure.

Specific or functional description with respect to embodiments disclosed herein according to the concept of the present disclosure is intended to merely explain the embodiments according to the concept of the present disclosure, and the embodiments according to the concept of the present disclosure may be embodied in various forms and are not limited to the embodiments described herein.

Since various changes may be made and several forms may be embodied in the embodiments according to the concept of the present disclosure, the embodiments are intended to be illustrated in the drawings and described in detail herein. However, the embodiments according to the concept of the present disclosure are not limited to the specific embodiments set forth herein, and include all changes, equivalents, or substitutes included in the spirit and technical scope of the present disclosure.

Terms such as 'first' and 'second' may be used to describe various components, but they should not limit the various components. Those terms are only used for the purpose of differentiating a component from other components. For example, a first component may be referred to as a second component, and a second component may be referred to as a first component and so forth without departing from the spirit and scope of the present disclosure. Furthermore, 'and/or' may include any one of or a combination of the components mentioned.

When it is mentioned that one component is "connected" or "accessed" to another component, it may be understood that the one component is directly connected or accessed to the other component or that still another component is interposed therebetween. In the meantime, when it is mentioned that one component is "directly connected" or "directly accessed" to another component, it may be understood that no component is interposed therebetween. Other expressions describing the relation between components, for example, "between" and "immediately between," or "adjacent to" and "directly adjacent to" should also be interpreted similarly.

Terms used herein are provided for merely explaining specific embodiments of the present disclosure, not limiting the disclosure. As used herein, the singular forms "a," "an" and "the" are intended to include the plural forms as well, unless the context clearly indicates otherwise. It will be understood that the terms "comprises" or "has" when used in this specification, specify the presence of stated features, integers, steps, operations, elements, components, or a combination thereof, but do not preclude the presence or addition of one or more other features, integers, steps, operations, elements, components, or a combination thereof.

Furthermore, unless defined otherwise, all the terms used in this specification including technical and scientific terms have the same meanings as would be generally understood by those skilled in the related art. The terms defined in generally used dictionaries should be construed as having the same meanings as would be construed in the context of the related art, and unless clearly defined otherwise in this specification, should not be construed as having idealistic or overly formal meanings.

Figure 2:
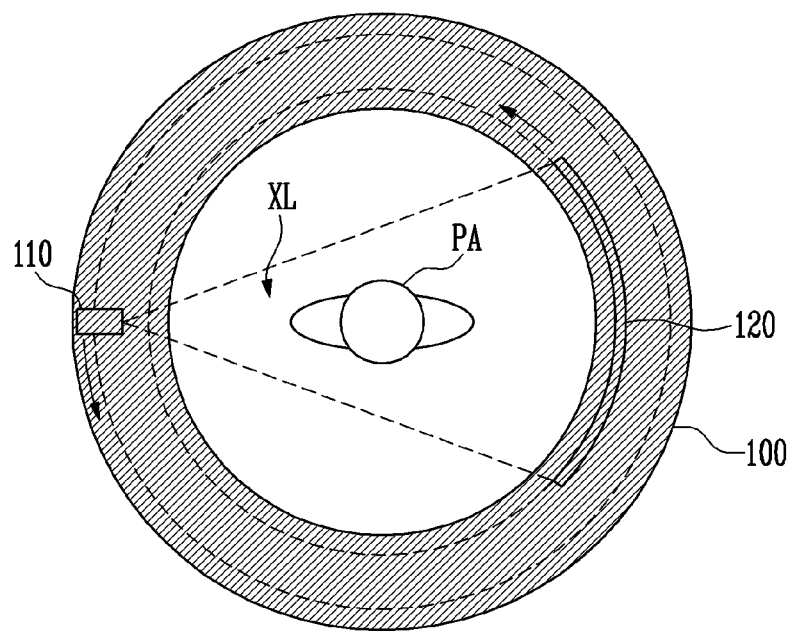
FIG. 2 is a conceptual diagram of a radiography apparatus according to an embodiment of the present disclosure.

FIG. 1 is a drawing for explaining an operation of a radiography apparatus according to an embodiment of the present disclosure, and FIG. 2 is a conceptual diagram of a radiography apparatus according to an embodiment of the present disclosure.

Referring to FIG. 1, a radiography apparatus 100 according to an embodiment of the present disclosure may capture an internal image of a subject PA using radiation. In other words, the radiography apparatus 100 irradiates the subject PA with the radiation and senses the radiation passed through the subject PA to generate an internal image of the subject PA.

For example, the radiography 100 may be, but is not limited to, any one of a digital radiography (DR) apparatus, a computed tomography (CT) apparatus, and a mammography apparatus.

In addition, the subject PA may be a living thing such as a human, an animal, or a plant, or an inanimate matter such as an object.

Referring to FIG. 2, the radiography apparatus 100 may include an X-ray source 110 for irradiating a subject PA with radiation XL and a sensing module 120 for sensing the radiation XL having passed through the subject PA to generate an internal image of the subject PA.

The X-ray source 110 and the sensing module 120 may rotate around the subject PA at every constant period inside the radiography apparatus 100. The X-ray source 100 may irradiate the subject PA with the radiation XL for a certain period in a rotating or stopped state and the sensing module 120 may be synchronized with the X-ray source 100 to sense the radiation XL having passed through the subject PA in a rotating or stopped state.

According to embodiments, the X-ray source 110 and the sensing module 120 may be disposed opposite to each other with the subject PA centered inside the radiography apparatus 100.

The radiography apparatus 100 according to embodiments of the present disclosure may control the X-ray source 100 such that the X-ray source 100 may emit the radiation XL only during a specific time period. Accordingly, the radiography apparatus 100 according to embodiments of the present disclosure may control emission of the radiation XL from the X-ray source 110 to generate an internal image of the subject PA in a more rapid speed.

By using the radiation XL emitted for a short time while rotating without stop, the radiography apparatus 100 according to embodiments of the present disclosure may generate an internal image of the subject PA in which a moving blur phenomenon is improved.

In addition, since using an X-ray tube as an electric field emitting source, the radiography apparatus 100 according to embodiments of the present disclosure is quicker in activating or deactivating the emission of the radiation XL than a typical radiography apparatus that uses heated thermal electrons.

According to embodiments, the radiography apparatus 100 may irradiate the subject PA with radiation XL having a pulse width of 8 ms or narrower.

In this way, the radiography apparatus 100 according to embodiments of the present disclosure may generate an internal high-definition image of the subject PA by using the X-ray source 110, which generates the radiation XL in correspondence to a high speed pulse.

Figure 3:
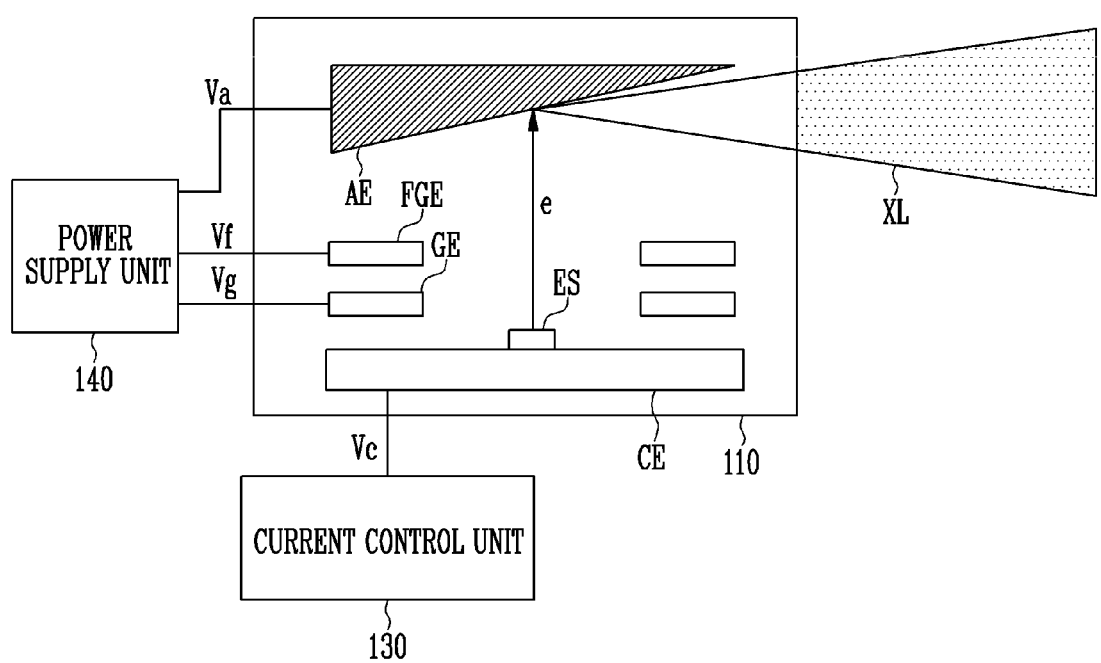
FIG. 3 is a drawing for explaining an X-ray source, a current control unit and a power supply unit according to embodiments of the present disclosure.

FIG. 3 is a drawing for explaining an X-ray source, a current control unit and a power supply unit according to embodiments of the present disclosure.

Referring to FIG. 3, the radiography apparatus 100 may include the X-ray source 110, a current control unit 130 for controlling an operation of the X-ray source 110, and a power supply unit 140.

The X-ray source 110 may include an anode electrode AE, a gate electrode GE, a focusing gate electrode FGE, and a cathode electrode CE.

The anode electrode AE may accelerate electrons e emitted from an electric field emitting source ES and generate the radiation XL using the emitted electrons e.

The gate electrode GE may induce electron emission from the electric field emitting source ES.

The focusing gate electrode FGE may focus the electrons e emitted by the gate electrode GE in a direction of the anode electrode AE.

Each of the anode electrode AE, the gate electrode, and the focusing gate electrode FGE may be connected to the power supply unit 140 to respectively receive an anode voltage Va, a gate voltage Vg, and a focusing gate voltage Vf.

The cathode electrode CE may be disposed to face the anode electrode AE and include the electric field emitting source ES for emitting the electrons e. The cathode electrode CE may be connected to the current control unit 130 to control an amount of electrons emitted from the electric field emitting source ES and a time when the electrons e are emitted.

The X-ray source 110 according to an embodiment of the present disclosure may be driven in a positive manner in which the cathode electrode CE is grounded and a positive voltage is applied to the anode electrode AE.

The X-ray source 110 according to another embodiment of the present disclosure may be driven in a negative manner in which the anode electrode AE is grounded and a negative voltage is applied to the cathode electrode CE.

The X-ray source 110 according to still another embodiment may be driven in a bipolar manner in which a third electrode (e.g. the gate electrode GE or the focusing gate electrode FGE), which exists between the anode electrode AE and the cathode electrode CE, is grounded, a positive voltage is applied to the anode electrode, and a negative voltage is applied to the cathode electrode CE.

Figure 4:
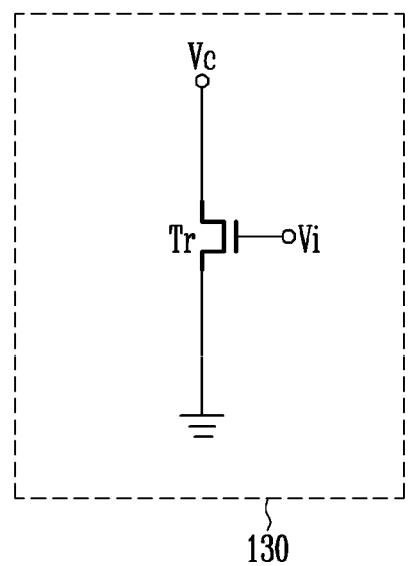
FIG. 4 is a schematic configuration diagram of the current control unit of FIG. 3 according to an embodiment of the present disclosure.

FIG. 4 is a schematic configuration diagram of the current control unit of FIG. 3.

Referring to FIG. 4, the current control unit 130 includes a switching transistor Tr, which is capable of controlling a current flowing between the cathode electrode CE and the anode electrode AE, and a first electrode of the switching transistor Tr may be connected to the cathode electrode CE, a second electrode thereof may be connected to a ground power source GND, and a gate may be connected to a switching voltage Vi.

According to an embodiment, the switching transistor Tr may be implemented with a field effect transistor (FET). However it is not limited thereto and the switching transistor Tr may also be implemented with a semiconductor device which performs a similar function.

In addition, the first and second electrodes of the switching transistor Tr may respectively correspond to the drain and source of the FET.

When a switching voltage Vi at a turn-on level is supplied to the gate of the switching transistor Tr, the switching transistor Tr connects the cathode electrode CE and the ground power source, and as the cathode electrode CE is grounded, the electric field emitting source ES may emit electrons.

According to an embodiment, when the switching transistor Tr is driven in a saturation region, the electric field emitting source ES may emit the electrons e uniformly due to a current limiting effect. Accordingly, the X-ray source 110 may maintain constantly the intensity of the radiation XL emitted to the subject PA.

The current control unit 130 may adjust a supply time of the switching voltage Vi such that the electric field emitting source ES may emit the electrons e for a short time.

For example, the current control unit 130 supplies the switching voltage Vi at the turn-on level for 8 ms or shorter to control the electric field emitting source ES to emit the electrons e for 8 ms or shorter.

When the switching voltage Vi at a turn-off level is supplied to the gate of the switching transistor Tr, the switching transistor Tr blocks the connection between the cathode electrode CE and the ground power source, and the electric field emitting source ES stops emitting the electrons e. At this point, the withstanding voltage of the switching transistor Tr may be designed to withstand a high voltage of the cathode electrode CE, which is raised by emission of the electrons e.

In FIG. 4, it is described that the cathode electrode CE is connected to the ground power source when the switching transistor Tr is turned on. However, the embodiment is not limited thereto, and the current control unit 130 according to an embodiment may control a current flowing through the cathode electrode CE such that the electrons e are emitted, even if the cathode voltage Vc is 0 V or higher.

Figure 5:
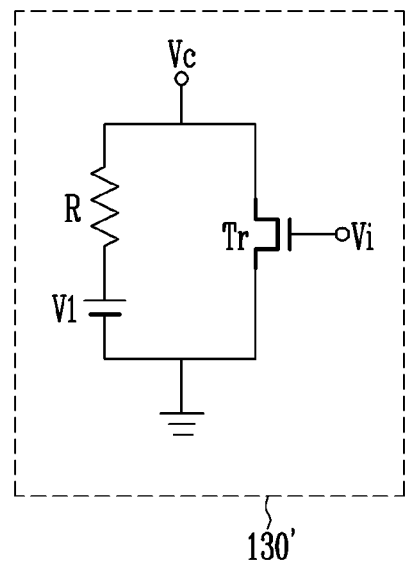
FIG. 5 is a schematic configuration diagram of the current control unit of FIG. 3 according to an embodiment of the present disclosure.

FIG. 5 is a schematic configuration diagram of the current control unit of FIG. 3.

Referring to FIG. 5, the current control unit 130 may include a pull-up voltage source V1, a pull-up resistor R, and a switching transistor Tr.

The pull-up voltage source V1 may be connected between the pull-up resistor R and the ground power source and may be connected to the cathode electrode CE through the pull-up resistor R to control an amount of the emitted electrons.

A first electrode of the switching transistor Tr may be connected to the cathode electrode CE, a second electrode thereof may be connected to the ground power source GND, and the gate electrode GE may receive the switching voltage Vi. The switching transistor Tr may be turned on or turned off according to the switching voltage Vi supplied to the gate electrode GE.

According to an embodiment, the switching transistor Tr may be any one of a PMOS transistor and an NMOS transistor.

For example, when the switching transistor Tr is the NMOS transistor, the switching transistor Tr may be turned on at the time of receiving the switching voltage Vi at a high level to connect the ground power source GND and the cathode electrode CE, and may be turned off at the time of receiving the switching voltage Vi at a low level to block the connection between the ground power source GND and the cathode electrode CE.

The X-ray source 110 according to an embodiment of the present disclosure may emit the electrons e from the electric field emitting source ES and may use the emitted electrons e to generate radiation XL, while the switching transistor Tr is turned on to ground the cathode electrode CE.

In addition, the X-ray source 110 according to an embodiment of the present disclosure may block the emission of the electrons e from the electric field emitting source ES to stop generating the radiation XL, while the switching transistor Tr is turned off.

Figure 6:
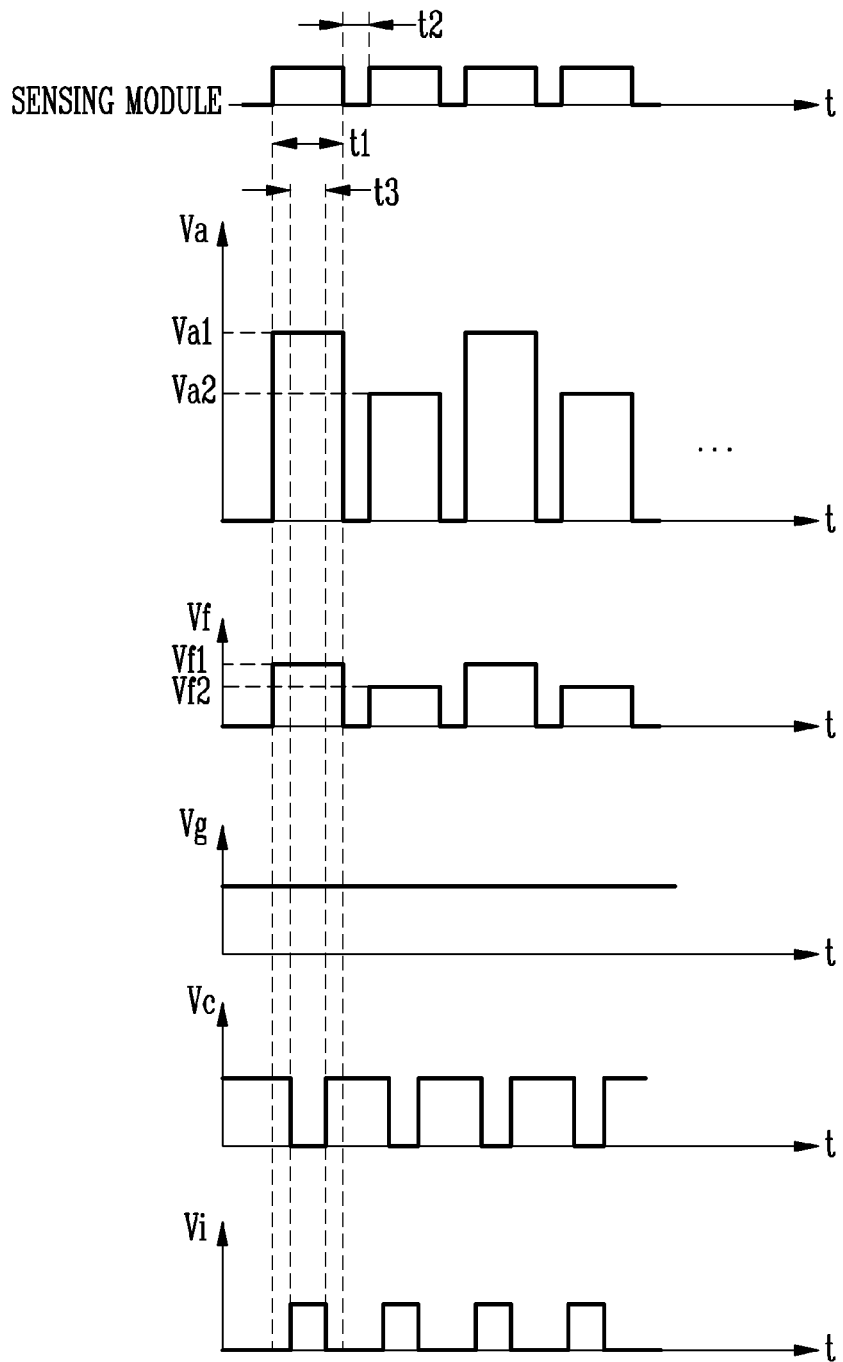
FIG. 6 is a timing diagram for explaining an operation method of an X-ray source according to an embodiment of the present disclosure.

FIG. 6 is a timing diagram for explaining an operation method of an X-ray source according to an embodiment of the present disclosure.

Referring to FIG. 6, graphs respectively show level changes of the anode voltage Va, the focusing gate voltage Vf, the gate voltage Vg, the cathode voltage Vc, and the switching voltage Vi, and activation periods t1 and non-activation periods t2 of the sensing module 120.

The sensing module 120 according to an embodiment of the present disclosure may sense the radiation XL having passed through the subject PA during the activation period t1 and may stop sensing the radiation XL during the non-activation period t2.

The radiography apparatus 100 may maintain the anode voltage Va and the focusing gate voltage Vf at a high level such that the X-ray source 110 irradiates the subject PA with the radiation XL during the activation period t1.

In addition, the radiography 100 may vary the anode voltage Va and the focusing gate voltage Vf to adjust acceleration energy of the electrons and a focusing voltage of the electron beam according thereto.

For example, the radiography apparatus 100 may supply any one of a first focusing gate voltage Vf1 and a second focusing gate voltage Vf2 to the focusing gate electrode FGE and any one of a first anode voltage Va1 and a second anode voltage Va2 to the anode electrode AE to adjust the acceleration energy of the electrons and the focusing voltage of the electron beam according thereto.

The X-ray source 110 may supply the gate voltage Vg at a constant level to the gate electrode GE during the activation periods t1 and the non-activation periods t2. At this point, as the gate voltage Vg, a sufficiently high voltage may be applied so that the current control unit 130 may limit the emission current.

In addition, the X-ray source 110 may supply the switching voltage Vi at a high level to the switching transistor Tr during a constant period t3 within the activation period t1 and may generate the radiation XL during a certain period. At this point, when the X-ray source is driven in a positive manner, the cathode electrode CE is connected to the ground power source GND to maintain a ground voltage.

Furthermore, during the remaining period of the certain period, the switching voltage Vi at a low level is supplied to the switching transistor Tr to turn off the switching transistor Tr, the cathode electrode CE may maintain an electric potential of a high level. At this point, the X-ray source 110 may stop generating the radiation XL.

Here, for the convenience of explanation of the present disclosure, it is assumed that the switching transistor Tr is an NMOS transistor, when the X-ray source 110 is driven in the positive manner. However, the radiography apparatus 100 may also emit the radiation XL in the negative manner and the bipolar manner, and in an identical method using the switching transistor Tr implemented with a PMOS transistor.

In addition, in FIG. 6, for the convenience of explanation, it is illustrated that the anode voltage Va and the focusing gate voltage Vf are dropped to 0 V during the non-activation period t2, but according to embodiments, the anode voltage Va and the focusing gate voltage Vf may maintain previous voltages without being dropped during the non-activation period t2.

Figure 7:
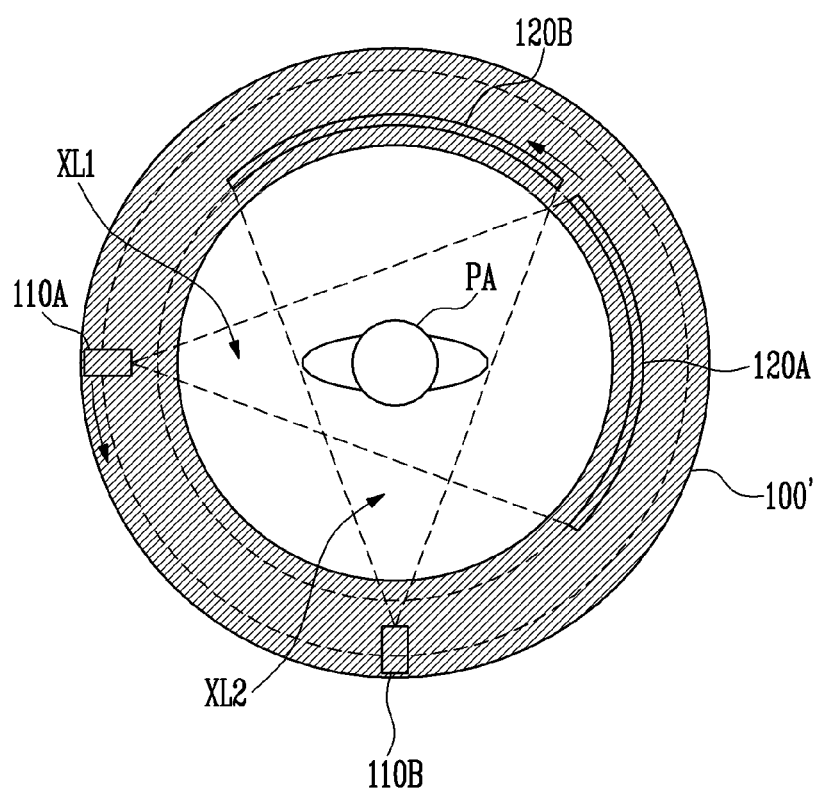
FIG. 7 is a conceptual diagram of a radiography apparatus according to another embodiment of the present disclosure.

FIG. 7 is a conceptual diagram of a radiography apparatus according to still another embodiment of the present disclosure.

A first X-ray source 110A and a second X-ray source 110B illustrated in FIG. 7 perform similar functions to those of the X-ray source 110 illustrated in FIG. 2, and a first sensing module 120A and a second sensing module 120B illustrated in FIG. 7 perform similar functions as those of the sensing module 120 illustrated in FIG. 2. Therefore overlapping descriptions thereabout will be omitted and like reference numerals will be used for like elements performing like functions.

Referring to FIG. 7, the radiography apparatus 100' may include the first X-ray source 110A for irradiating a subject PA with first radiation XL1, a second X-ray source 110B for irradiating the subject PA with second radiation XL2, a first sensing module 120A for sensing the first radiation XL having passed through the subject PA and a second sensing module 120B for sensing the second radiation XL2 having passed through the subject PA.

The first and second X-ray sources 110A and 110B may be disposed with a certain interval therebetween, the first X-ray source 110A and the first sensing module 120A may be disposed opposite to each other with the subject PA centered inside the radiography apparatus 100', and the second X-ray source 110B and the second sensing module 120B may be disposed opposite to each other with the subject PA centered inside the radiography apparatus 100'.

The first and second X-ray sources 110A and 110B and the first and second sensing modules 120A and 120B may rotate around the subject PA at every constant period inside the radiography apparatus 100'.

The first and second X-ray sources 110A and 110B respectively irradiate the subject PA with the first and second radiations XL1 and XL2 in a stop state for a certain period, and the first and second sensing modules 120A and 120B may respectively sense the first and second radiations XL1 and XL2 having passed through the subject PA while the first and second X-ray sources 110A and 110B irradiate the subject PA with the first and second radiations XL1 and XL2 in the stop state.

According to embodiments, the first X-ray source 110A may emit the first radiation XL1 during a first period and the second X-ray source 110B may emit the second radiation XL2 during a second period after the first period. At this point, the first radiation XL1 and the second radiation Xl2 may be set to have the same intensity or different intensities.

Figure 8A:
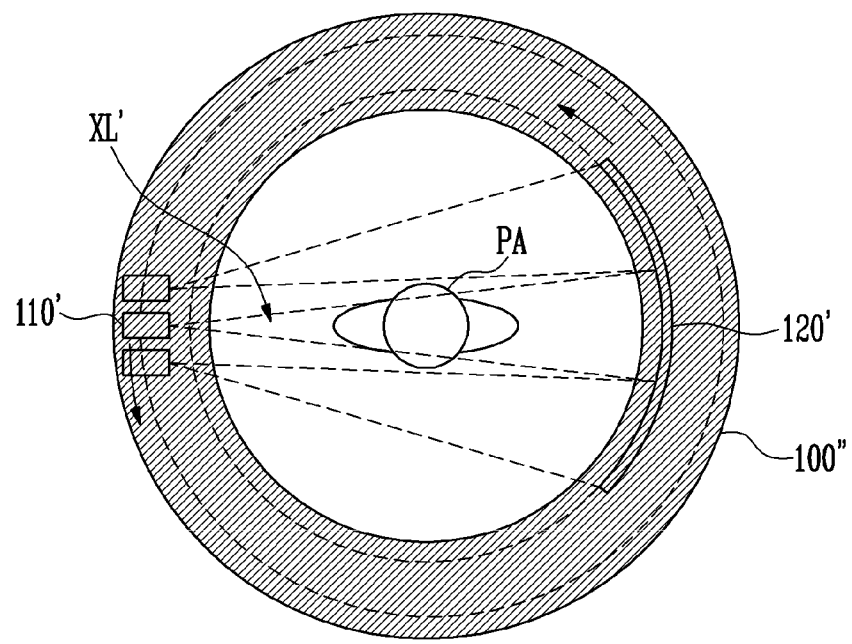
FIGS. 8A and 8B are conceptual diagrams of a radiography apparatus according to further another embodiment of the present disclosure.
Figure 8B:
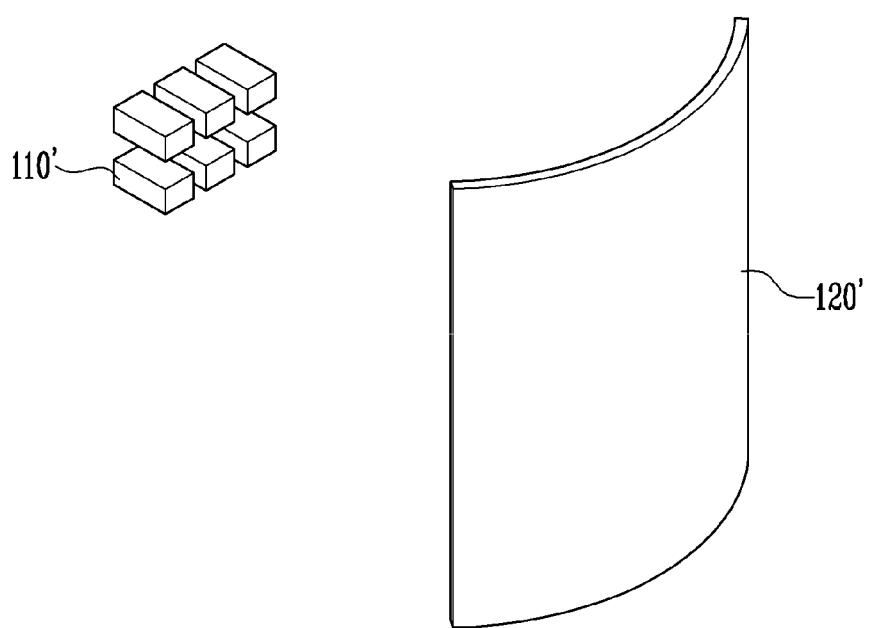

FIGS. 8A and 8B are conceptual diagrams of a radiography apparatus according to further another embodiment of the present disclosure.

Since the X-ray sources 110' illustrated in FIGS. 8A and 8B perform similar functions to those of the X-ray source 110 illustrated in FIG. 2 and the sensing modules 120' illustrated in FIGS. 8A and 8B perform similar functions to those of the sensing module 120 illustrated in FIG. 2, overlapping descriptions thereabout will be omitted.

Referring to FIG. 8A, each of the X-ray sources 110' may irradiate the subject PA with radiation. Each of the X-ray sources 110' may irradiate a specific region of the subject PA with the radiation XL' at a narrow radial angle and the sensing module 120' may combine the radiations XL' emitted from the X-ray sources 110' to generate an image of the entire subject PA.

At this point, since the radiations XL' emitted from the X-ray sources 110' may interfere with each other, when any one of the X-ray sources 110' emits the radiation XL', other adjacent X-ray sources 110' may stand by without emitting the radiations XL'.

Referring to FIG. 8B, the X-ray sources 110' may be disposed in an n×m array, where n and m are integers.

For example, the X-ray sources 110' may be disposed in 2×3 array to be opposite to the sensing module 120'. At this point, the X-ray sources 110' may adjust the radial angle of the emitted radiation XL' to image a specific region of the subject PA and the sensing module 120' may generate the entire image of the subject PA with a combination of the radiations XL' emitted from the X-ray sources 110'.

In addition, in FIGS. 8A and 8B, a method is described in which one sensing module 120' senses the radiations XL' emitted from the X-ray sources 110', but the method is not limited thereto. The radiography apparatus 100'' according to an embodiment of the present disclosure may include a plurality of sensing modules 120' and the plurality of sensing modules 120' may sense the radiations XL' emitted from the X-ray sources 110' to generate an image of the subject PA.

According to a radiography apparatus of the present disclosure, a subject's internal image in which a moving blur phenomenon is improved may be generated using radiation emitted while rotating without stop for a short time.

In addition, since the radiography apparatus of the present disclosure uses an X-ray tube as an electric field emitting source, emission of radiation may be activated or deactivated in a more rapid speed in comparison to a typical radiography apparatus that uses heated thermal electrons.

In addition, the radiography apparatus of the present disclosure may vary energy to adjust the intensity of radiation, and accordingly density classification of a subject may be easily understood and the internal structure of the subject may be more clearly imaged.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A radiography apparatus comprising:
an X-ray source configured to irradiate a subject with radiation; and
a sensing module configured to sense the radiation having passed through the subject,
wherein the X-ray source comprises:
a cathode electrode comprising an electric field emitting source configured to emit electrons;
an anode electrode disposed opposite to the cathode electrode and configured to use the electrons to generate the radiation; and
a current control unit connected to the cathode electrode to control an amount of the electrons,
wherein the current control unit comprises:
a switching transistor of which a first electrode is connected to the cathode electrode, a second electrode is connected to a ground power source, and a gate electrode receives a switching voltage; and
a pull-up voltage source connected to the cathode electrode through a serially connected pull-up resistor to control an amount of the electrons.

2. The radiography apparatus according to claim 1, wherein the X-ray source and the sensing module rotate around the subject at every constant period.

3. The radiography apparatus according to claim 1, wherein the X-ray source further comprises a gate electrode configured to induce emission of the electrons from the electric field emitting source.

4. The radiography apparatus according to claim 3, wherein the X-ray source further comprises a focusing gate electrode configured to focus the electrons emitted by the gate electrode.

5. The radiography apparatus according to claim 1, wherein the X-ray source irradiates the subject with the radiation when the switching transistor is turned on.

6. The radiography apparatus according to claim 1, wherein the switching transistor is driven in a saturation region according to a supply of the switching voltage.

7. The radiography apparatus according to claim 1, further comprising:
a power supply unit configured to supply an anode voltage to the anode electrode,
wherein the power supply unit varies the anode voltage at every constant period.

8. The radiography apparatus according to claim 1, wherein the X-ray source and the sensing module are disposed opposite to each other with the subject centered.

9. The radiography apparatus according to claim 1, further comprising a power supply unit configured to supply an anode voltage to the anode electrode and a focusing gate voltage to a focusing gate electrode of the X-ray source,
wherein the power supply unit varies the anode voltage and the focusing gate voltage simultaneously.

10. A radiography apparatus comprising:
a first X-ray source configured to irradiate a subject with first radiation;
a second X-ray source separately disposed from the first X-ray source at a given interval to irradiate the subject with second radiation;
a first sensing module configured to sense the first radiation having passed through the subject; and
a second sensing module configured to sense the second radiation having passed through the subject,
wherein each of the first X-ray source and the second X-ray source comprises:
a cathode electrode comprising an electric field emitting source configured to emit electrons;
an anode electrode disposed opposite to the cathode electrode and configured to accelerate the electrons; and
a current control unit connected to the cathode electrode to control an amount of the electrons, and
wherein the current control unit comprises:
a switching transistor of which a first electrode is connected to the cathode electrode, a second electrode is connected to a ground power source, and a gate electrode receives a switching voltage; and
a pull-up voltage source connected to the cathode electrode through a serially connected pull-up resistor to control an amount of the electrons.

11. The radiography apparatus according to claim 10, wherein each of the first X-ray source and the second X-ray source further comprises:
a gate electrode configured to induce emission of the electrons from the electric field emitting source; and
a focusing gate electrode configured to focus the electrons emitted by the gate electrode.

12. The radiography apparatus according to claim 10, wherein the first X-ray source emits the first radiation for a first period, and the second X-ray source emits the second radiation for a second period after the first period.

13. The radiography apparatus according to claim 12, wherein intensities of the first and second radiations are different from each other.

14. The radiography apparatus according to claim 10, wherein the first X-ray source and the first sensing module are disposed opposite to each other, and the second X-ray source and the second sensing module are disposed opposite to each other.

15. A radiography apparatus comprising:
a first X-ray source configured to irradiate a subject with first radiation;
a second X-ray source separately disposed from the first X-ray source at a given interval to irradiate the subject with second radiation; and
a sensing module configured to sense the first and second radiations having passed through the subject,
wherein each of the first X-ray source and the second X-ray source comprises:
a cathode electrode comprising an electric field emitting source configured to emit electrons;
an anode electrode disposed opposite to the cathode electrode and configured to accelerate the electrons; and
a current control unit connected to the cathode electrode and to control an amount of the electrons, and
wherein the current control unit comprises:
a switching transistor of which a first electrode is connected to the cathode electrode, a second electrode is connected to a ground power source, and a gate electrode receives a switching voltage; and
a pull-up voltage source connected to the cathode electrode through a serially connected pull-up resistor to control an amount of the electrons.

16. The radiography apparatus according to claim 15, wherein the first X-ray source and the second X-ray source are disposed opposite to the sensing module.

* * * * *